United States Patent [19]

Levene

[11] Patent Number: 5,209,232
[45] Date of Patent: May 11, 1993

[54] BIOPSY NEEDLE POSITIONING

[75] Inventor: Simha Levene, Doarna Hadarom, Israel

[73] Assignee: Elscint Ltd., Haifa, Israel

[21] Appl. No.: 648,846

[22] Filed: Jan. 31, 1991

[30] Foreign Application Priority Data

Jan. 30, 1990 [IL] Israel .................. 093215

[51] Int. Cl.$^5$ .................. A61B 6/00
[52] U.S. Cl. .................. 128/653.1; 378/37; 364/413.14
[58] Field of Search .................. 128/653.1, 654, 659; 378/16, 17, 37, 108; 364/413.14

[56] References Cited

U.S. PATENT DOCUMENTS

| | | | |
|---|---|---|---|
| 4,570,264 | 2/1986 | Liebetruth | 378/20 |
| 4,821,727 | 4/1989 | Levene et al. | 128/653.1 |
| 4,907,152 | 3/1990 | Lempriere | 364/413.14 |
| 5,003,571 | 3/1991 | Kido et al. | 378/37 |
| 5,078,142 | 1/1992 | Siczek et al. | 378/37 |
| 5,081,357 | 1/1992 | Agano | 378/37 |
| 5,105,457 | 4/1992 | Glassman | 378/37 |

FOREIGN PATENT DOCUMENTS 2545396  4/1977  Fed. Rep. of Germany ........ 378/37
2203620 10/1988  United Kingdom ............ 364/413.14

OTHER PUBLICATIONS

"Mammographic Needle Localization of Lesions Seen in Only One View", American Journal of Radiology, R. Yagan et al., vol. 144, pp. 911-916, May 1985.

Primary Examiner—Lee S. Cohen
Assistant Examiner—K. M. Pfaffle
Attorney, Agent, or Firm—Sandler Greenblum & Bernstein

[57] ABSTRACT

A mammalary biopsy needle positioning scheme that improves on the system of U.S. Pat. No. 4,821,727. In the present invention, the arrival of the needle holder into a pixel is distinguished by comparing latest data per pixel to average data per pixel. If the comparison reveals marked differences from the average value, then the average value is discarded and the new data is used whereas in the absence of marked differences, the new data is averaged with the old average. The result is images with highlighted needle holder insertion information thereby providing images of the needle holder in the breast in a much shorter time than provided by the prior art and/or with smaller X-ray doses.

7 Claims, 1 Drawing Sheet

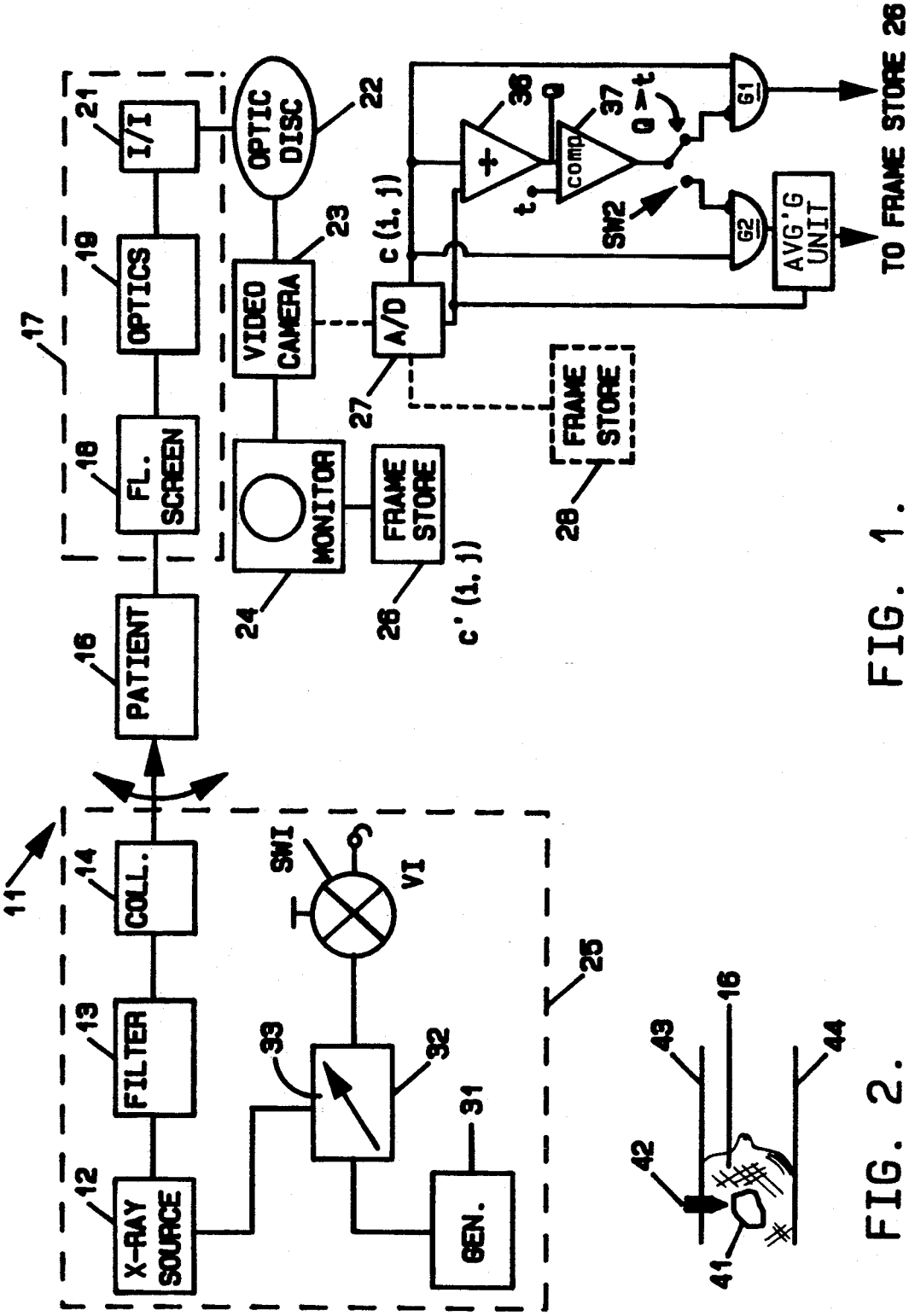

BIOPSY NEEDLE POSITIONING

FIELD OF THE INVENTION

This invention is concerned with radiographic imaging systems and more particularly with such systems used to assist in safely locating growths for a surgeon performing mammallary biopsy procedures.

BACKGROUND OF THE INVENTION

X-rays have long been used to acquire images of the interior of the patient's body for diagnostic purposes. More recently, X-ray equipment has been used for assisting in invasive techniques, such as biopsies and lithotripsy. For example, in X-ray mammography the breast of the patient is X-rayed and X-ray films are used to determine whether there are any micro-calcifications or other growths (hereinafter generally termed "lesions"). If a lesion is discovered then it is necessary to determine if the lesion is benign or if it requires immediate treatment. For such a determination, it is often necessary to perform a biopsy. To assist the surgeon in locating the lesion for the biopsy, the radiologist inserts a radio opaque needle holder adjacent to the growth. A barbed needle is then inserted through the holder into the center of the suspected growth and the needle holder is removed. The point of the needle indicates to the surgeon the exact location of the tissue to be excised.

In greater detail, with the prior art systems, the patient was brought to the mammographic X-ray system. The patient's breast was compressed between horizontal plates attached to the X-ray equipment with a C-arm. The C-arm is a "C" shaped bracket which normally holds the X-ray tube at the top of the "C" and the X-ray beam receptor at the bottom of the "C". The radiologist marked the breast or one of the compression plates at a point in the plane where he thought the lesion was located based on the study of a preliminary X-ray. A new X-ray image was then taken and developed to determine whether the marking was indeed in the correct location. If the marking was not in the correct location, then the radiologist repeated the marking procedure and acquired another X-ray image. When the marking was indeed aligned with the lesion, then the radiologist inserted the needle holder into the compressed breast through an aperture or recess in the compression plate at the marked point so as to center the needle tip within the lesion.

The breast was then removed from compression plate and the C-arm was rotated 90°. The breast was again compressed but now with the compression plates vertically aligned. Still another X-ray was acquired to check the alignment of the needle holder tip and lesion in the vertical plane to assure that the holder tip was in the proper location. If the holder tip was not within the lesion the needle holder was moved and another image was acquired. The process was repeated until coincidence between views was obtained.

Then the needle was inserted into the holder and the holder was withdrawn leaving the needle pointing out the exact location of the lesion for the surgeon.

Thus, in prior art X-ray mammography a multiplicity of X-ray images and a plurality of breast clamping operations were required to position the needle to locate the lesion for the surgeon. The repeated operations besides being time-consuming and uncomfortable for the patient, also subjected the patient to the relatively substantial X-ray dosage required to acquire the many images.

Radiologists and scientists were and are seeking to improve the biopsy needle positioning procedure. For example, in March, 1984, a presentation at the National Conference on Breast Cancer of the American College of Radiation described a technique for mammographic needle localisation of lesions which cannot be imaged in two orthoginal views, but only in one of them. In the described technique, the X-ray beam is moved 30° in a xeromammographic system where there is no breast clamping. An article describing the presentation appeared in "The American Journal of Radiology", Vol. 144, pp. 911–916, in May of 1985. The article describes a method that does not use C-arm clamping whereby it is possible to locate the needle using images taken at two positions, 30° apart.

In the past mammographic compression devices for X-ray film mammographic systems used what may be described as "dependent compression". At the top of the C-arm, there was an X-ray tube and collimator arrangement which served as the source of the X-ray beam. A cone extended from the source to the breast to compress the breast against the X-ray radiation receptor or film at the bottom of the C-arm. A removable X-ray film container was provided at the other side of the compression means.

Rotating the C-arm also rotated the compression means. Subsequently, movable compression plates were attached to the C-arm between the X-ray source at the top of the C-arm and the X-ray receptor (i.e. the film) at the other end. The movable compression plates were removably attached along the longitudinal axis of the C-arm to adjust to the woman's breast. In this arrangement, the compression plates rotate with the C-arm. Thus, this arrangement also required unclamping and reclamping the breast when the C-arm was rotated even through small angles.

Compression plates are important in mammography. They improve the quality of the image and thereby enable the discovery of more lesions. When the breast is compressed, it flattens and absorbs less X-ray beams and it absorbs the X-ray beams more uniformly. In addition, extraneous movements are eliminated. These beneficial results of clamping improve the quality of the image. Therefore, it is highly desirable to compress the breast for mammograph breast image processing.

From the above description of the prior art, it is readily understood that it would save time and reduce patient discomfort if a system could be provided that generates an immediate image to aid in positioning the lesion-locating needle holder for biopsy purposes. It would save further time and discomfort if it could utilize a single clamping position and avoid movements of the lesion during reclamping with the consequent relative movement of needle holder and lesion.

These functions are provided in the system described in U.S. Pat. No. 4,821,727 which issued on Apr. 18, 1989, and is assigned to the Assignee of this Patent Application. That Patent describes a system using an imaging chain rather than film for determining the location of the needle holder and also uses a clamping means that does not require reclamping of the breast when the source of the X-rays is moved to obtain another perspective view needed to absolutely locate the needle holder in the interior of the breast. The system described herein improves on the patented system in that, among other things, it provides for obtaining the image of the needle holder in less time than was required with the patented system.

Thus, an object of the system described herein is to position the biopsy needle in a minimum of time with a minimum of X-ray dosage and maximum of accuracy.

BRIEF DESCRIPTION OF THE INVENTION

In accordance with the present invention, a mammographic biopsy needle holder positioning system is provided, said system comprising:

X-ray source means for emitting X-ray beams directed to pass through the breast of the patient, collimating means for limiting the X-rays passing through the breast to a small area, breast compression means for compressing the breast in a direction to decrease and make uniform the path length in the breast through which the X-rays beams pass, X-ray receptor means on the side of the breast opposite the X-ray source means for receiving said X-ray beams after passage through the compressed breast, means for tilting said X-ray source means a sufficient amount to obtain parallax views of a biopsy needle holder inserted into the breast, said breast compression means being uncoupled from said means for tilting said X-ray source means, image processing means coupled to said receptor means to process said received X-ray beams to obtain image data per unit area corresponding to pixels in a display image (said unit area hereafter called "pixel"), means for averaging the image data acquired per pixel, means for comparing newly acquired data per pixel to the average data per pixel for determining any marked difference between the value of the average acquired data per pixel and the newly acquired X-ray data per pixel, means responsive to a marked difference between the value of average acquired data per pixel and the value of the newly acquired X-ray data per pixel for discarding the value of the average acquired data per pixel and using instead the value of the newly acquired X-ray data per pixel, means responsive to there being no marked difference between the value of the average of the acquired data per pixel and the value of the newly acquired X-ray data per pixel for averaging the value of the newly acquired X-ray data per pixel into the value of the average acquired X-ray data per pixel thereby improving the image while the newly acquired data per pixel indicates the insertion into the breast of a needle holder that has a different radio transmission characteristic than the tissue of the breast.

Accordingly, a feature of the invention focuses on distinguishing the insertion of the needle holder into a pixel of the breast and utilizing the X-ray data per pixel caused by the needle in the path of the X-ray beam as new data not to be averaged with the tissue data of that pixel thereby obtaining an image of the needle in the breast in a much shorter time than previously accomplished.

Biopsy positioning needle holders presently available are highly opaque to X-rays (high radio opaqueness). A relatively small X-ray exposure is sufficient to image the needle holder well enough to enable accurate placement with respect to the breast tissue provided that a good quality image of the tissue is preserved.

It is a feature of the invention to use at least one frame store to accumulate X-ray data per pixel of the image of the tissue and to also accumulate the exclusive X-ray data of the radio opaque needle holder to the exclusion of the tissue imaging data acquired for the same pixel before the needle holder entered the pixel.

According to another feature of the invention, the imaging chain utilizes a very small charge coupled device (CCD) as the camera. Such devices are now commercially available with $1024 \times 1024$ or $4096 \times 4096$ areas corresponding to image pixels.

In the event that a biopsy localization needle holder having a high radio transparency is used, the invention would also apply except that the inventive system would have to be informed that the needle holder being used was radio transparent rather than radio opaque.

The system completely updates only those pixels in a digital image of the breast that change substantially because of needle insertion. The other pixels are cummulatively improved.

The system of the invention uses X-ray doses that are much smaller than in the above noted patent. In fluoroscopic performed mammography, the image is quantum noise limited. Therefore, the total X-ray dose required until the fluoroscopic image has sufficient quality to unequivocably identify the suspected region normally is equal to that required for photographic imaging. Even though biopsies are carried out on a high risk section of the population, it is desirable to reduce this total radiation dose.

The object of the present invention is to provide means to facilitate biopsy needle insertions and/or other biopsy procedures including removal of pathological tissue by suction exactly as described in the above cited Patent; i.e., by viewing the region of interest successively from two angles using high resolution (150 line pairs (1p) per cm) X-ray fluorescence techniques but at much reduced patient dose. To achieve this aim, the proposed device makes use of the dependence of visual contrast in the image upon object contrast. Biopsy localization needle holders are typically metallic having a very high (X-ray) contrast to the tissue background. Thus, the needle holder can be identified easily even in a low quality image resulting from using very low X-ray exposure techniques.

A feature of the present invention makes use of the dependence of the visual image contrast upon object's size. A biopsy localization needle holder typically has a cross section of say 1 mm. This is resolved by the viewer at much lower visual contrast than the individual nodules of a micro-calcification cluster, many of which are smaller than 0.2 mm diameter. Thus, the radiologist can use a lower exposure factor to find and position the needle holder. The tissue portions of the image are being continuously reinforced by new data so that the image that is finally obtained clearly identifies both the growth and the needle holder in much less time and using much fewer exposures to X-rays than was obtainable in the above noted Patent.

BRIEF DESCRIPTION OF THE DRAWINGS

The above mentioned and other features and objects of the present invention will be best understood when considered in the light of the following description made in conjunction with the accompanying drawings, wherein:

FIG. 1 is a block diagram showing the system for selective averaging of newly acquired X-ray data or insertion of newly acquired X-ray data, and FIG. 2 is a cross sectional view of the patient's breast between compressing plates showing a needle holder inserted therein.

GENERAL DESCRIPTION

The inventive mammographic biopsy needle holder system 11 of FIG. 1 includes an X-ray source 12 having a filter 13 between the X-ray source and the patient. A collimator 14 selectively limits the X-rays from the source to a relatively small section of the patient, in this case the compressed breast of the patient shown at 16. Preferably the X-ray source is a micro-focused type X-ray tube. The collimator has a small aperture, not shown, which can be used; since, the X-ray beam merely has to encompass the lesion in the breast and a small area around the lesion. The small size encompassed by the X-ray beam improves image quality by minimizing scatter. It also reduces the dose to which the patient is subjected. The source is movable so that different views of the lesion may be acquired to assure properly locating the needle holder in the breast through the use of views at parallax angles.

An imaging chain 17 is provided so that an immediate image can be viewed during "stops" while the needle holder is inserted into the breast toward the lesion. The image chain includes fluorescent screen 18 which fluoresces when struck by X-ray beams to form an inchoate image. An optical system 19 directs the image on the fluorescent screen 18 to an image intensifier 21.

In a preferred embodiment, the X-ray source is a small focus tube (0.3 mm FS typically at 55 cms. source-to-image distance). The X-ray detector; i.e., fluorescent screen has at least a one inch diameter sensitive area (field of view) and preferably has a 2 inch diameter field of view which facilitates positioning the needle holder at the lesion.

While electronic X-ray detectors may be used within the scope of the invention, a preferred embodiment uses a high DQE fluorescence screen such as those used in mammographic film screen cassettes with 150 to 200 line pairs per cm resolution. The optical system 19 may include a lens or a reducing fiber optic arrangement. The image intensifier preferably is a micro-channel imaging intensifier with sensitive area matching the sensitive area of the fluorescent screen and having a resolution equivalent to that of the screen. The microchannel image intensifier is superior to the electron beam tube type image intensifier because it is much shorter thereby also facilitating the radiologist's manipulations of the needle holder, but more importantly because the image in the intensifier has a very high spatial stability—an essential feature of the needle holder positioning for lesion location.

The image intensifier output is directed to an optical distributor 22 and from the optical distributor 22 to a video camera 23. The optical distributor, in a preferred embodiment, is a lens system which may include an image splitter.

It should be understood that other means could be provided for directing the image from the image intensifier to the video camera. For example, there could be direct coupling between the image intensifier and the video camera.

The image sensor of the TV camera may be a vacuum tube, for example, a vidicon. However, it is preferable to employ a charge coupled device (CCD) detector because such a detector is physically much smaller than the vaccum tube equipped detectors available. The CCD enables the radiologist to manipulate the needle holder with greater ease. In addition, the CCD detector has superior spatial stability, an essential feature of the system. Also, commercial CCDs are available having 1024×1024 or 4098×4098 pixels. Thereby, carrying an image of a 150 line pairs per centimeters over a 5 cm diameter.

It should further be noted that an image intensifier is needed in the system only if the image sensor will otherwise introduce image noise at a higher level than X-ray quantum noise.

The output of the video camera is directed to a display monitor 24. The data per pixel comprising the image is stored in a frame store shown at 26. The frame store facilitates freezing the image on the display monitor in addition to storing the cummulative average value per pixel. The analog data of the video camera is transformed to digital data by an analog-to-digital converter unit 27. It is the digital data that is provided to each pixel for constructing the image on the display monitor 24.

The X-ray system 25 is powered by a high voltage generator shown at 31. Such generators are well known and are commonly used in mammography and typically provide an exposure of 80 mA for 4/10ths of a second at 27 KVp, having an additional facility for exposures at much smaller tube currents such as, for example, 8 mA in place of the 80 mA, or for much shorter times say 10 mS, or for a continuous fluorescence exposures at very low currents indeed, in a neighborhood of about 2 mA.

The same frame store 26 is used for holding the average X-ray data per pixel used in making up the images on the display monitor 24. In the event that processing of the data is not sufficiently fast in the system, a second frame store 28 may be provided into which the newly acquired image data is stored. The second frame store is shown in dotted line form. It receives input from the analog-to-digital converter 27.

Means preferably are provided for incrementing the dosage applied to the X-ray tube 12. More particularly, the incrementing means is shown at 32 while the arrow at 33 indicates that either the time of exposure can be varied and/or the intensity of the exposure can be varied. The exposure is incremented responsive to the operation of switch SW1 by the radiologist. The operation of the switch SW1 causes the X-ray source 12 to emit X-rays for the set time and/or X-rays with a set intensity by connecting an enabling voltage V1 to the incrementing means 32.

Means are provided for determining whether to average the newly acquired X-ray data per pixel into the average of the previously acquired data, or whether to merely use the newly acquired data for imaging purposes without first averaging the newly acquired with the previously acquired data. More particularly, as shown in FIG. 1, the newly acquired data from the analog-to-digital converter unit 27 is indicated as C(i,j). This data is provided into one input of divide unit 36. The other input of the dividing unit 36 is the average of previously acquired data per pixel indicated as C'(i,j). Say, for example, that the newly acquired data is used as the divisor and the averaged previously acquired data is the dividend, then the quotient (Q) at the output of the divide unit 36 is connected to comparator 37. The other input of the comparator is a threshold value t that is selected by the radiologist. If a radiation opaque type needle holder is in the path of the X-ray beam, the newly acquired data will be smaller than the previously acquired data and the threshold value t will be greater than 1 (such as, for example, 1.2 or 1.5). So, when the quotient is higher than the threshold value (say 1.3) the switch means SW2 is directed to couple the output of the comparator 37 to the enable input of gate G1. The output of gate G1 goes to frame store 26. There is no averaging done, it goes directly to the frame store 26. Thus, when the value of Q is greater than the threshold t (indicating that a high radio or opaque device, such as the needle holder, has entered into the pixel) then the newly acquired data is written directly into the frame store.

When the quotient is less than or equal to the threshold, then switch SW2 directs the output of the comparator to the enable input of gate G2. The gate G2 then directs the newly acquired data into an averaging unit 38 where it is averaged with the average of all previously acquired data for that pixel. The output of the averaging unit is written into the frame store to replace the previous averaged X-ray data of the particular pixel.

Thus, X-ray data of tissue is cummulatively averaged in unit 38 and inserted into frame store 26 to be used in providing the data for an image on monitor 24. Thus, each incremental dose of X-ray improves the image of the tissue. Each incremental dose of X-ray also clearly shows any advancement made in the needle holder because the image immediately indicates the X-ray data for the needle holder alone and not averaged with tissue. The new data results in a display of the needle holder and clearly indicates where the needle holder is relative to the lesion. The lesion can be marked by an arrow or an X by the central processing unit (CPU) controlling the operation of the system.

One preferred embodiment uses a personal computer (PC) for a CPU Each incremental X-ray exposure improves the image of the lesion, therefore, the radiologist does obtain a good view of the lesion, an excellent view of the needle holder and its exact position.

FIG. 2 is a cross sectional view of the compressed breast indicating the lesion 41 and the needle holder 42. The compression plates are shown at 43 and 44. The needle holder is moved into the breast towards the lesion. Imaging is not done during the movement of the needle holder to avoid artifacts that would be caused, among other things, by displacement of the tissue as the needle holder moves. Thus, the operator inserts the needle a small distance, takes an X-ray by operating switch SW1, looks at the display, moves the needle a little more, increments an X-ray dosage by applying another dose. Each new dose improves the basic image of the lesion and clearly shows each new position of the needle holder 42.

It should be understood that if a radio transparent needle holder is used, such as for example, a needle holder of polyethylene which is more transparent than tissue to X-rays, then the threshold rather than being greater than 1 would be less 1 (such as 0.8 for example) and the same results would be obtained. The X-ray values stored in the frame store are proportional to the value of the charge on the area of the CCD detector that corresponds to a pixel of the image. This X-ray value is the value obtained during the exposure interval which in a preferred embodiment is the standard TV interval of 65 microseconds. It is, of course, possible to utilize longer intervals.

When the comparator indicates that the X-ray data is from tissue, then cumulative averaging is performed with the previous average data for a particular pixel. When the comparator indicates that the X-ray data is from a radio opaque device then the data is used as fresh data without averaging.

At the end of the exposure interval, the ratio of the fresh signal data $C(i,j)$ to the previously obtained average signal is compared to a threshold. If the ratio or the quotient is less than the threshold, then $C'(i,j)$ is updated by averaging the fresh data with the existing data; i.e., $C''(i,j)$ is made equal to $[n*C'(i,j)+C(i,j)]/(n+1)]$. At the same time the integral number of the pixel $n(i,j)$ which is stored in a separate "frame integral number memory" in the computer is increased by 1, such that $n(i,j)=n(i,j)+1$.

In operation, the system is used as follows:

The breast is clamped into the compression device with the region of interest in the center of the field of view; so that involuntary patient motion does not blur the image.

With the X-ray tube head tilted, an image is acquired either by a single exposure at high current (for example, 80 mA for 0.5 secs at 27 KVp), or in the fluorescent mode; i.e., with the X-ray tube continuously operated at low current, (for example, 4 mA) and the imaging screen updated at standard TV (65 microseconds) intervals. The image will be accumulated in the pixels until the operator determines that the exposure time has been long enough to acquire adequate image quality.

A marker may be used to identify the target, to which the needle is to be brought. An electronic zoom may also be used if desirable.

The X-ray head is tilted to the opposite cant and the operations are repeated.

The radiologist determines from the image where to initiate the insertion of the needle holder. The needle holder is partially inserted in the position and at the angle determined by the radiologist.

The image is updated in a fluoroscopic mode until the target and the end of the needle can both be clearly seen using the display. The needle is then guided into the target by incrementally updating the image. It is important not to operate the X-ray source when the needle is in motion. Instead, the X-rays are used between needle movement to provide excellent imaging on a low dose budget.

While the invention is described in a specific embodiment, it should be understood that this embodiment as described by way of example only and not as any limitation on the scope of the invention.

What is claimed is:

1. A mammographic biopsy needle holder positioning system for positioning a needle holder to locate lesions in a patent's breast, said system comprising:
    a biopsy needle holder adapted to be inserted into the breast, said needle holder having a different X-ray transmission characteristic than body tissue,
    an X-ray source for generating X-ray beams directed to pass through the breast of the patient,
    an X-ray detector located opposite the X-ray source for detecting said X-ray beams after the X-ray beams traverse the breast and providing output signals,
    a processor for processing the output signals of the X-ray detector to provide display data giving views of the interior of the breast, compression plates for compressing the breast substantially in the direction of the X-ray beams, means for averaging said display data to obtain averaged display data, means for providing a display from said averaged display data, said processor including storage means for storing the average display data per pixel which is used to provide the display, comparison means for comparing data acquired last for a particular pixel to the averaged display data for the particular pixel to determine whether said data acquired last for the particular pixel is substantially the same as the averaged display data for the particular pixel, first gate means connected to said comparison means for averaging the data acquired last with the averaged display data for the particular pixel, and second gate means connected to said comparison means for providing the data acquired last to said storage means as new display data for the pixel without averaging with the prior obtained averaged data.

2. The mammographic biopsy needle holder positioning system of claim 1 wherein said comparison means for comparing comprises:

a divider for dividing the averaged display data for the particular pixel by the data acquired last for the particular pixel to provide a quotient, and a comparator for providing a comparison between the quotient of the divider to a threshold greater than or equal to "1", when said needle holder is more opaque to X-rays than is body tissue, and means responsive to the comparison for averaging the data acquired last with the averaged data for the particular pixel when the comparison shows that the data acquired last is equal to or larger than the threshold.

3. The mammographic biopsy needle holder positioning system of claim 1 wherein said comparison means for comparing comprises:

a divider for dividing the data acquired last by the averaged acquired data for the particular pixel to provide a quotient, means for comparing the quotient of the divider with a threshold less than or equal to "1" when the needle holder is less opaque to X-rays than normal body tissue, and means responsive to the comparison for averaging the data acquired last with the averaged data for that particular pixel when the comparison shows that said quotient is less than or equal to the threshold.

4. The mammographic biopsy needle holder positioning system of claim 1, wherein said comparison means for comparing comprises:

a divider providing a quotient by dividing the data acquired last by the averaged data for the pixel, a comparator for comparing the quotient with a threshold that is more than or equal to "1" to provide a comparison, means responsive to said comparison showing that said quotient is more than said threshold for discarding the averaged data for a particular pixel and entering said data acquired last for the particular pixel in said storage means.

5. The mammographic biopsy needle holder positioning system of claim 1 including tilting means for tilting the X-ray source and said detector includes means for obtaining images of the breast at different angles, and said tilting means tilts independently of said compression plates.

6. The mammographic needle holder positioning system of claim 1 wherein said X-ray detector comprises:

a fluorescent screen for providing a fluoroscopic image, an image intensifier coupled to said fluorescent screen for providing an output that is an intensified fluoroscopic image, a video camera for providing an output of inchoate display data, optical means for coupling said video camera to the output of said image intensifier and, said processor being coupled to the output of the video camera to process that inchoate display data to provide the display data.

7. The system of claim 6 wherein said image intensifier comprises a charge coupled device.

* * * * *